United States Patent [19]
Olsen

[11] Patent Number: 4,508,824

[45] Date of Patent: * Apr. 2, 1985

[54] PSEUDOMONAS DEGRADATION OF HYDROCARBONS

[75] Inventor: Ronald H. Olsen, Ann Arbor, Mich.

[73] Assignee: Microlife Technics, Inc., Sarasota, Fla.

[*] Notice: The portion of the term of this patent subsequent to Feb. 15, 2000 has been disclaimed.

[21] Appl. No.: 436,077

[22] Filed: Oct. 22, 1982

Related U.S. Application Data

[63] Continuation-in-part of Ser. No. 147,563, May 8, 1980, Pat. No. 4,374,200.

[51] Int. Cl.$^3$ .................... C12N 15/00; C12N 1/20; C12N 1/00; C12P 19/34; C12R 1/38
[52] U.S. Cl. .................... 435/172.3; 435/91; 435/253; 435/317; 435/874; 935/29; 935/52; 935/59; 935/72
[58] Field of Search ............ 435/172, 253, 317, 874, 435/875, 876, 877, 91, 172.3

[56] References Cited

U.S. PATENT DOCUMENTS

| | | |
|---|---|---|
| 3,813,316 | 6/1972 | Chakrabarty . |
| 4,259,444 | 3/1981 | Chakrabarty . |
| 4,374,200 | 2/1983 | Olsen ........................... 435/68 |

OTHER PUBLICATIONS

Novick, Bact. Rev. 33:210-235(1969).
Jacoby et al, Nature, 274:179-180(1978).
Holloway, B. W., Bacteriological Reviews, 33, 419-443 (1969).
Vandenbergh et al, Appl. and Environ. Microbiol., 42:737-739, 1981.
Olsen et al, J. Bacteriol 123:28-35 (1975).
Atlas, R. H., Microbiol. Rev. 45:180-209 (1981).
Olsen, J. Bacteriol. 133:210-216(1978).

*Primary Examiner*—Thomas G. Wiseman
*Assistant Examiner*—James Martinell
*Attorney, Agent, or Firm*—Ian C. McLeod

[57] ABSTRACT

Selected new bacteria of the genus Pseudomonas, particularly the species *Pseudomonas putida* and *Pseudomonas aeruginosa*, which have the ability to utilize organic compounds from the generic groups aliphatic, cyclo aliphatic, aromatic and/or polynuclear aromatic hydrocarbons are described. The source of genetic materials facilitating degradation of the aromatic compounds are metabolic plasmids. In particular, *Pseudomonas putida* or other Pseudomonas obtained from soil samples and having a non-transmissible and stable ability to degrade hexane (as well as related aliphatic hydrocarbons) are used as starting strains to produce the new bacteria. Transconjugal mating and selection for these genetic traits resulted in the production of bacteria capable of utilizing representative compounds of all the generic groups of the previously listed organic compounds. The bacteria are useful for waste degradation.

11 Claims, 3 Drawing Figures

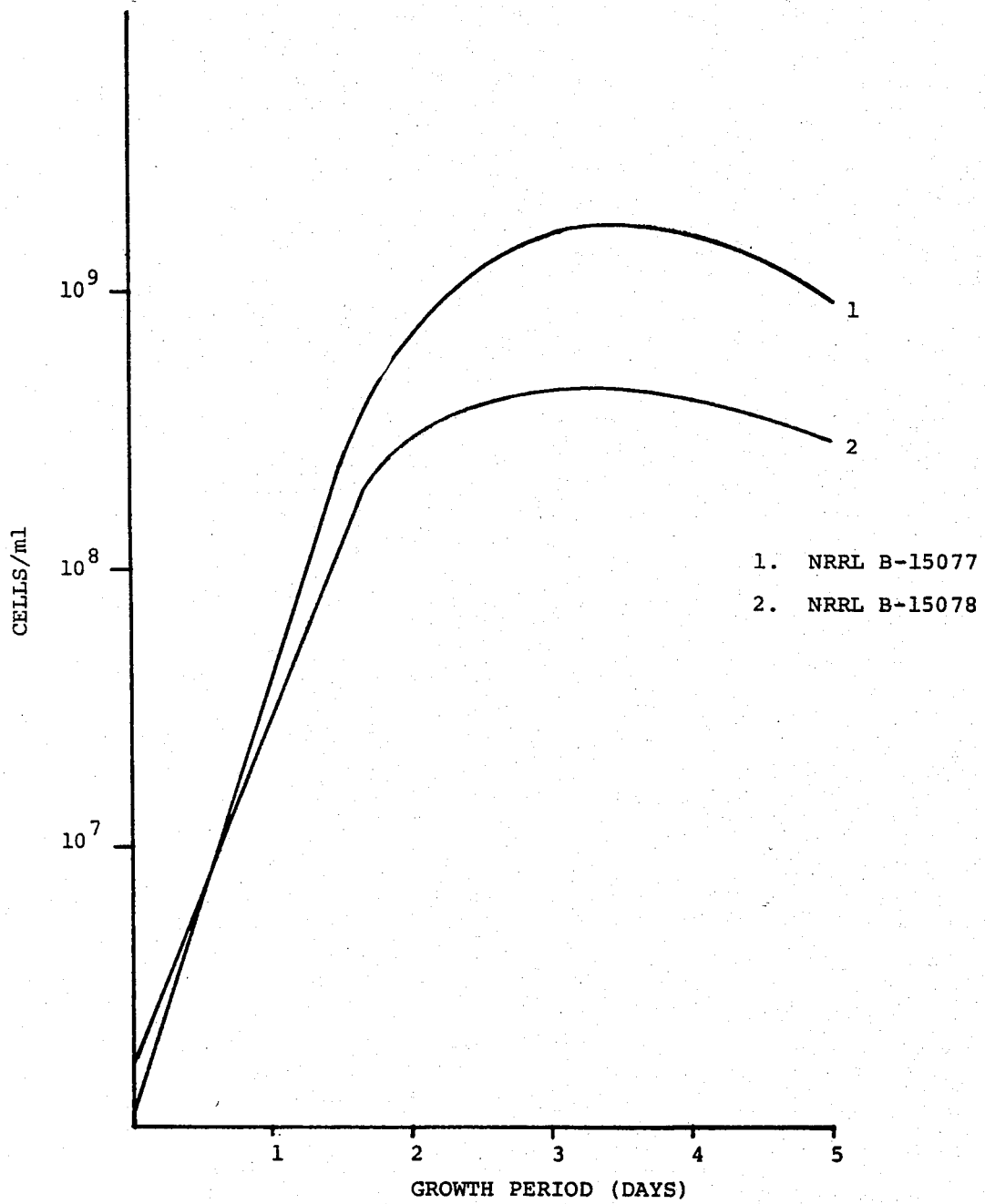

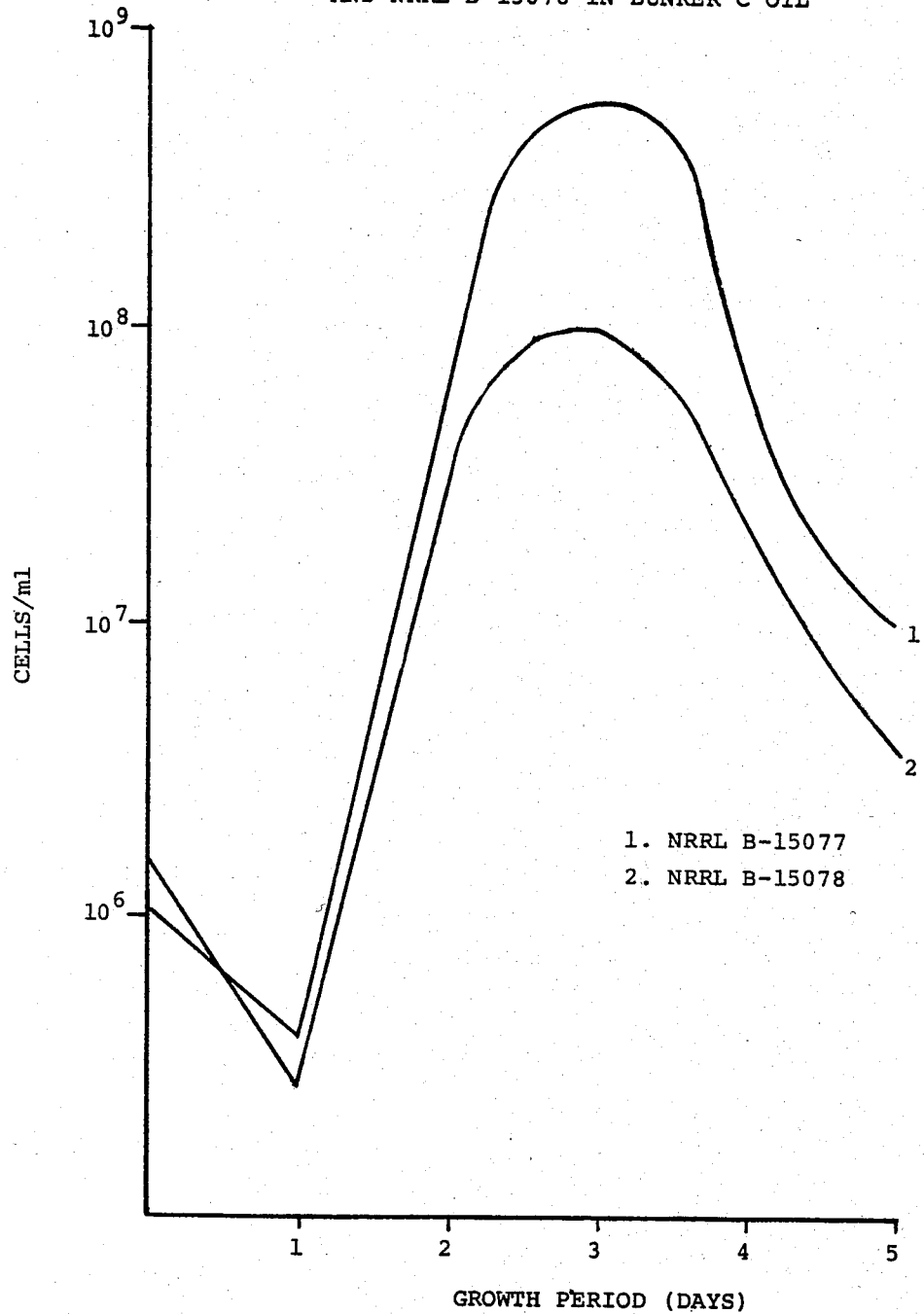

PSEUDOMONAS DEGRADATION OF HYDROCARBONS

CROSS-REFERENCE TO RELATED APPLICATION

This application is a continuation-in-part of U.S. Patent application Ser. No. 147,563, filed May 8, 1980 now U.S. Pat. No. 4,374,200.

SUMMARY OF THE INVENTION

1. Background of the Invention

A method is described for genetically transforming Pseudomonas bacteria, to provide diverse genotypical capability for the degradation of organic compounds in a single strain by incorporating plasmids derived from disparate sources.

*Pseudomonas putida*, is a Pseudomonas strain having a non-plasmid capability of degrading aliphatic compounds is used as a starting strain. In particular, a *Pseudomonas putida* strain was found which utilizes aliphatic hydrocarbons (hexane) of varied length as a sole source of its carbon and energy. A naphthalene (NPL) plasmid and other plasmids specifying the degradation of camphor (CAM) and toluene (TOL) are genetically introduced into the bacterium which utilizes the aliphatic hydrocarbons (HEX) through transconjugal mating. The result is in the construction of a single bacterial strain with all these metabolic activities which is stable such that the capability is not lost as the strain is propagated and used.

2. Prior Art

U.S. Pat. Nos. 3,813,316 and 4,259,444 to Chakrabarty describe Pseudomonas bacteria containing multiple plasmids and a method for their preparation. Basically the method provides for transconjugal mating and fusion of plasmids in the cells of the recipient bacterium so the plasmids are stable and can be replicated as the cells grow and divide. This method uses ultraviolet light for the fusion; however, other methods are for instance recombination between plasmids as described by Novick, Bact. Rev. 33:210-23q(1969) and transposition of regions of a plasmid as described by Jacoby et al., Nature, 274:179-180(1978).

Chakrabarty described novel Pseudomonas bacteria which contain both aliphatic and aromatic pathways together. This was accomplished by providing plasmids in the Pseudomonas which degraded both classes of compounds. The problem is that the Chakrabarty Pseudomonas does not provide stable or reliable aromatic and/or aliphatic hydrocarbon degradation, probably because of a reversion of the fused plasmids to a non-fused condition due to a basic instability.

In the method of transferring the hydrocarbon degrading metabolic plasmids by transconjugal mating, the plasmid donor bacterium is mutated or otherwise selected to require a nutrient factor, particularly an amino acid, as a "marker" for growth. The recipient is a bacterium selected to be able to grow without the donor nutrient factor and/or with an antibiotic resistance factor so that the recipient produced by the mating with the plasmids can be selected. Sometimes the donor or recipient bacterium also has other factors which allow for selection of one or the other. It would be very desirable if methods could be provided which facilitate the transfer of the plasmids to the recipient bacterium and which provides for ease of selection using a nutrient factor and an antibiotic resistance factor.

OBJECTS

Therefore it is an object of the present invention to provide novel Pseudomonas, particularly *Pseudomonas putida*, wherein the aliphatic hydrocarbon degrading characteristic is non-transmissible by transconjugal mating and is stable. Further, it is an object of the present invention to provide methods which use plasmid vectors which are derivatives of pRO1600 as shown in FIG. 1, particularly plasmid vectors pRO1601 or pRO1614, during transconjugal mating. These and other objects will become increasingly apparent from the following description and the drawings.

IN THE DRAWINGS

FIGS. 2 and 3 show growth rates for the new NRRL-B-15078 strain in heavy oils and in Bunker C oil in comparison to the starting strain NRRL-B-15077.

GENERAL DESCRIPTION

Figure 1:
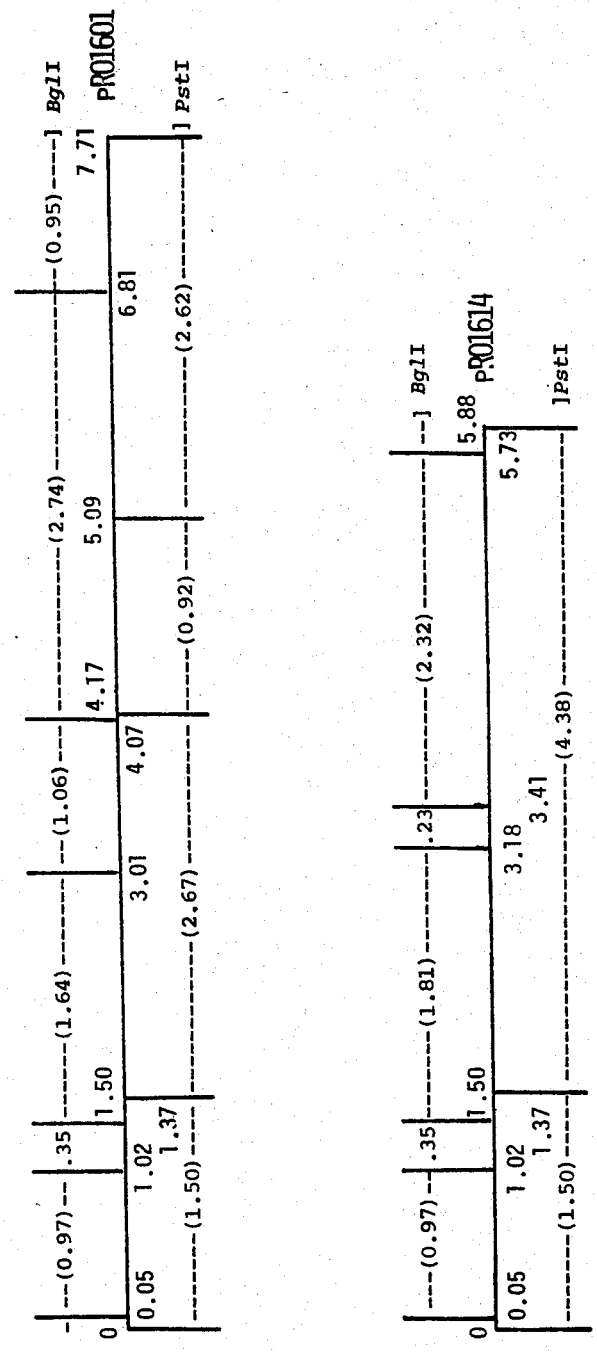
FIG. 1 is an endonuclease restriction enzyme map of pRO1601 and the pRO1614 derivative thereof used in the present invention, wherein the fragment sizes are measured in kilobase pairs.

The present invention relates to a bacterium of the genus Pseudomonas containing at least one stable metabolic plasmid which provides an aromatic hydrocarbon degradative pathway and wherein the strain has the non-transmissible and stable ability to degrade hexane. The present invention also relates to a bacterium of the genus Pseudomonas containing an aromatic hydrocarbon energy generating metabolic plasmid and a derivative of pRO1600 as carried in NRRL-B-12124 along with RPl, particularly pRO1601 or pRO1614 as shown in FIG. 1.

The present invention further relates to a method of introducing hydrocarbon degrading metabolic plasmids into a bacterium of the genus Pseudomonas by transconjugal mating to transmit the plasmid of a donor bacterium to a recipient bacterium to produce a transconjugant bacterium containing the metabolic plasmid, wherein the recipient and donor bacterium are each different nutrient factor auxotrophs, the improvement which comprises:

(a) providing a donor bacterium containing (1) a plasmid derivative of pRO1600 as carried in NRRL-B-12124; and (2) at least one first series hydrocarbon degrading metabolic plasmid wherein each metabolic plasmid derives energy from different aromatic hydrocarbons;

(b) mating the donor bacterium with a recipient bacterium to produce a first transconjugant bacterium without the pRO1600 plasmid derivative and with the metabolic plasmid; and (c) growing the transconjugant bacterium with the nutrient factor required by the recipient bacterium without the nutrient factor required by the donor bacterium so as to isolate the first transconjugant bacterium with the metabolic plasmid of the donor bacterium. The present invention also includes the additional step of conjugally mating the first transconjugant bacterium so as to introduce at least one additional hydrocarbon degrading metabolic plasmid as a second series with the first series plasmid to produce a second transconjugant bacterium containing at least two hydrocarbon degrading metabolic plasmids which are from the first and second series of such metabolic plasmids.

The present invention also relates to a method of introducing hydrocarbon degrading metabolic plasmids into a bacterium of the genus Pseudomonas by transconjugal mating to transmit the plasmid of a donor bacterium to a recipient bacterium to produce a transconjugant bacterium containing the metabolic plasmid, wherein the recipient and donor bacterium are each different nutrient factor auxotrophs the improvement which comprises:

(a) providing a donor bacterium containing at least one first series hydrocarbon degrading metabolic plasmid;

(b) providing a recipient bacterium containing a plasmid derivative of pRO1600 as carried in NRRL-B-12124 wherein the plasmid derivative includes an antibiotic resistance marker not present in the donor bacterium;

(c) mating the donor bacterium and the recipient bacterium to produce a transconjugant bacterium with the pRO1600 plasmid derivative and the metabolic plasmid; and (d) growing the transconjugant bacterium with the nutrient factor required by the recipient bacterium without the nutrient factor required by the donor bacterium in the presence of the antibiotic so as to isolate the transconjugant bacterium with the metabolic plasmid of the donor bacterium and the pRO1600 derivative.

The derivatives of pRO1600 which are described in parent application Ser. No. 147,563 which are used in the present invention are pRO1601 as carried in NRRL-B-12124 and pRO1614 as carried in NRRL-B-12125 as shown in FIG. 1. A more refined characterization of the endonuclease enzyme digestion fragments has resulted in the changes over parent application Ser. No. 147,563. This application describes other derivatives of pRO1600 which can be used.

The present invention thus particularly relates to providing methods and compositions including a preferably *Pseudomonas putida,* which contains plasmids which control the utilization of aromatic, including polynuclear aromatic hydrocarbons, and which has a non-transmissible and stable ability to degrade hexane and related aliphatic compounds. *Pseudomonas putida* with the appropriate plasmid can utilize the relevant aliphatic hydrocarbon as a sole source of energy and carbon for its growth and cellular synthesis. This bacterium is non-pathogenic and was derived from the soil environment before its improvement by the techniques of bacterial genetics. Obviously, other bacteria with these characteristics can be isolated.

SPECIFIC DESCRIPTION

A bacterium of the genus Pseudomonas which contains a conjugally transmissible plasmid which specifies components of a degradative pathway for the hydrocarbon naphthalene (NPL) was used as a starting strain. This strain, referred to as *Pseudomonas putida,* used subsequent to its isolation and characterization for genetic transfer of this activity, was isolated from a natural soil sample which had contained aromatic hydrocarbons for many years which allowed natural selection for the degradation of this compound. This strain is deposited with the Northern Regional Research Laboratory (NRRL) in Peoria, Ill. as NRRL-B-15138 and is freely available upon request by number. Another strain which was isolated from the same soil sample which specifies components of a degradative pathway for aliphatic hydrocarbons (C6 to C12) and is deposited with the NRRL as NRRL-B-15078. The bacterial strains were isolated by a procedure described previously for bacteria growing on halogen substituted aromatic hydrocarbons in application Ser. No. 310,090, filed Oct. 9, 1981, using tryptophan; however, other isolation means can be used. Observations of growth in various media, general group characterization tests and the determination of optimum conditions were as described previously in "The Aerobic Pseudomononands: A Taxonomic Study" by R. Stanier et al. Journal of General Microbiology 43:159-271 (1966).

*Pseudomonas aeruginosa* strain PAO was used as an intermediate bacterial host for the fusion of two plasmids and the transfer of the fusion product to other bacteria was as described previously in B. W. Holloway in 37 Genetics of Pseudomonas", Bacteriological Reviews, 33, 419–443 (1969) and is deposited as NRRL-B-15136. *Pseudomonas putida* strains containing respectively a plasmid specifying components for the degradation of toluene (TOL) or camphor (CAM) were received from Dr. James Shapiro, The University of Chicago and were labeled respectively PpS1142 (CAM) and PpS2116(TOL) and are deposited with the NRRL as NRRL-B-16065 and B-15066, respectively. These strains had been mutated by Shapiro to require the amino acid L-tryptophan for their growth as a marker.

The following Example illustrates the preparation by genetic conjugation of the bacterial strains and their plasmids to obtain a final resultant bacterial strain having a very diverse metabolic capability. The genetic donor and recipient bacterial strains, their relevant metabolic traits and the resultant genetic hybrid bacterial strains are shown in Table 1 and are discussed in detail hereinafter.

TABLE I

| Step | Bacterial Genetic Donor | Bacterial Recipient | Resulting bacterial Strain |
|---|---|---|---|
| 1 | Pp NRRL-B-15066 (TOL) Trp⁻ | PAO1c NRRL-B-15136 | PAO NRRL-B-15067 (TOL) |
| 2 | Pp NRRL-B-15065 (CAM) Trp⁻ | PAO2 Ser⁻ | PAO NRRL-B-15068 (CAM) Ser⁻ |
| 3 | PAO NRRL-B-15068 (CAM) Ser⁻ | PAO25 Leu⁻, Arg⁻ | PAO NRRL-B-15069 (CAM) Leu⁻, Arg⁻ |
| 4 | PAO NRRL-B-15069 (CAM) Leu⁻, Arg⁻ | PAE1.25 (pRO1601) Ser⁻, Cb$^r$ | PAONRRL-B-15137 (CAM/pRO1601) Ser⁻ Cb$^r$ |
| 5 | PAO NRRL-B-15137 (CAM/pRO1601) Ser⁻, Cb$^r$ | PAO25 Leu⁻, Arg⁻ | PAO NRRL-B-15071 (CAM/Tnl)Leu⁻, Arg⁻ Cb$^r$ |
| 6 | PAO NRRL-B-15071 (CAM/Tnl) Leu⁻ Arg⁻, Cb$^r$ | PAO NRRL-B-15067 (TOL) Ser⁻ | PAO NRRL-B-15072 (CAM/TOL) |
| 7 | PAO NRRL-B-15072 (CAM/TOL) | PAO NRRL-B-12127 (pRO1614) Ser⁻ Cb$^r$, Tc$^r$ | PAO NRRL-B-15073(CAM/TOL/pRO1614) |

TABLE I-continued

| Step | Bacterial Genetic Donor | Bacterial Recipient | Resulting bacterial Strain |
|---|---|---|---|
| 8 | PAO NRRL-B-15073(CAM/TOL/ pRO1614) Ser$^-$, Cb$^r$, Tc$^r$ | PAO25 Leu$^-$ Arg$^-$ | Ser$^-$, Cb$^r$, Tc$^r$ PAO NRRL-B-15074 (CAM/ TOL)Leu$^-$, Arg$^-$ |
| 9 | PAO NRRL-B-15074(CAM/TOL)Leu$^-$, Arg$^-$ | PAO2 Ser$^-$ | PAO NRRL-B-15075 (CAM/ TOL)Ser$^-$ |
| 10 | Pp NRRL-B-15138 (NPL) | Pp NRRL-B-15078 (HEX) | Pp NRRL-B-15076 NPL/HEX) |
| 11 | PAO NRRL-B-15075(CAM/TOL) Ser$^-$ | Pp NRRL-B-15076 (NPL/HEX) | Pp NRRL-B-15077 (CAM/ TOL/NPL/HEX |

PAO is *Pseudomonas aeruginosa*; Pp is *Pseudomonas putida*; CAM is camphor degrading plasmid; TOL is a toluene degrading plasmid.

In particular:

(1) Resulting Strain NRRL-B-15067. This strain was developed through a patch mating procedure described in Appl. and Environ Microbiol 42:737–739, 1981 at 30° C. The mating mixture *Pseudomonas putida* NRRL-B-15066 and PAO1c was plated onto minimal medium (mmo) in the presence of toluene (TOL) vapors. The resulting transconjugant PAO1c(TOL) NRRL-B-15067 was able to utilize toluene.

(2) Resulting Strain NRRL-B-15068. This strain was developed through a patch mating procedure of *Pseudomonas putida* NRRL-B-15065 and PAO2.

(3) Resulting Strain NRRL-B-15069. This strain was developed through a patch mating procedure. *Pseudomonas aeruginosa* NRRL-B-15068 was the genetic donor.

(4) Resulting Strain NRRL-B-15137. A screw cap tube mating was performed at 37° C., according to the method described in J. Bacteriol 123:28–35 (1975). This method involves the donor strain NRRL-B-15069 which was a leucine, arginine auxotroph of NRRL-B-15069 that contained the camphor (CAM) plasmid. The recipient strain was PAE1.25 a serine requiring auxotroph of NRRL-B-15136 containing plasmid pRO1601 as carried in NRRL-B-12125 with the transposon Tnl coding for carbenicillin (Cb$^r$) and ampicillin (Ap$^r$) resistance.

(5) Resulting Strain NRRL-B-15071. This strain was developed through an (A10) mating procedure, described in J. Bacteriol. 133:210–216 (1978) at 37° C. Section medium was glucose minimal salts (VBG) supplemented with leucine, arginine, and Cb$^{500}$. The resulting transconjugant was auxotrophic for leucine, arginine, and was also carbenicillin resistant (Cb$^r$).

(6) Resulting Strain NRRL-B-15072. A screw cap tube mating was accomplished using strains NRRL-B-15071 and PAO1c(RPl/TOL) at 30°. Selection was growth on minimal medium in the presence of camphor (CAM) crystals. The resulting transconjugant NRRL-B-15072 grew on camphor and p-toluate.

(7) Resulting Strain NRRL-B-15073. This strain was developed through a patch mating between strains NRRL-B-15072 and PAO2(pRO1614) plasmid as carried in NRRL-B-12127. The resulting transconjugant NRRL-B-15073 as selected for growth on mmo serine Tc$^{50}$ in the presence of toluene vapors. The transconjugant was also checked for camphor (CAM) utilization.

(8) Resulting Strain NRRL-B-15074. A patch mating was performed using NRRL-B-15073 and PAO25 at 30° C. The mating mixture was plated onto minimal media containing leucine, arginine and camphor crystals. The transconjugants were further examined for utilization of toluene (TOL).

(9) Resulting Strain NRRL-B-15075. A patch mating was accomplished between NRRL-B-15074 and PAO2 at 30°. The transconjugants were plated onto minimal media supplemented with serine, and camphor crystals. The transconjugants were further examined for growth in the presence of toluene.

(10) Resulting Strain NRRL-B-15076. A screw cap tube mating was performed at 28° C. The mating mixture was plated onto minimal media in the presence of naphthalene (NPL) crystals. The resulting transconjugant NRRL-B-15076 grew on naphthalene (NPL) and hexane (HEX).

(11) Resulting Strain NRRL-B-15077. A screw cap tube mating was performed at 25° C. using strains NRRL-B-15075 and NRRL-B-15076. The resulting transconjugant NRRL-B-15077, was able to utilize camphor (CAM), toluene (TOL), naphthalene (NPL) and hexane (HEX), for sole carbon and energy sources.

All of the strains in the preceeding example are deposited with the Northern Regional Research Laboratory of the USDA in Peoria, Ill. and are freely available on request by number.

EXAMPLE 2

Starting strain NRRL-B-15078 and new strain NRRL-B-15077 were grown in minimal salts medium containing heavy oil as the sole carbon and energy source. As depicted in FIG. 2, the NRRL-B-15077 strain grew at an increased rate when compared to the parental strain NRRL-B-15078. After the 5 day incubation period the strains were isolated and examined for their phenotypic traits. The isolate NRRL-B-15077 was able to utilize naphthalene, camphor, toluene and hexane as sole carbon and energy source.

EXAMPLE 3

Starting strain NRRL-B-15078 and new strain NRRL-B-15077 were grown in minimal salts medium containing Bunker "C" oil as the carbon and energy source. The initial decline at day 1, reflects the sticking of the bacterial cells to the tar balls present in the Bunker "C" oil as described by R. H. Atlas in Microbiol. Rev. 45:180–209, 1981.

After the 5 day incubation period strain NRRL-B-15077, was able to utilize naphthalene, camphor, toluene and hexane as sole carbon and energy source. These results suggest that the plasmids present in strain NRRL-B-15077 are stable even when they are grown in a medium not containing their preferential substrate.

As can be seen from the foregoing Examples the method of the present invention provides novel Pseudomonas strains which are useful as transconjugal bacterial intermediates or transconjugal bacterial products which have stable metabolic plasmids from diverse sources. The product bacteria are very useful for waste degradation.

I claim:

1. In a method of introducing hydrocarbon degradation encoding metabolic plasmids into a bacterium of the genus Pseudomonas by transconjugal mating to transmit the plasmid of a donor bacterium to a recipient bacterium to produce a transconjugant bacterium containing the metabolic plasmid, wherein the recipient and donor bacterium are each different nutrient factor auxotrophs the improvement which comprises:
   (a) providing a donor bacterium containing (1) a plasmid derivative of pRO1600 as carried in NRRL-B-12124 and (2) at least one first series hydrocarbon degradation encoding metabolic plasmid wherein each metabolic plasmid derives energy from different hydrocarbons;
   (b) mating the donor bacterium with a recipient bacterium to produce a first transconjugant bacterium without the pRO1600 plasmid derivative and with the metabolic plasmid; and
   (c) growing the transconjugant bacterium with the nutrient factor required by the recipient bacterium without the nutrient factor required by the donor bacterium so as to isolate the first transconjugant bacterium with the metabolic plasmid of the donor bacterium.

2. The method of claim 1 wherein the pRO1600 derivative is pRO1614 as carried in NRRL-B-12127.

3. The method of claim 1 wherein the pRO1600 derivative is pRO1601 as carried in NRRL-B-12125 and wherein pRO1601 facilitates the addition of an antibiotic marker in the recipient bacterium.

4. The method of claim 1 wherein the donor bacterium in step (a) contains the hydrocarbon degradation encoding metabolic plasmids CAM and TOL with the plasmid derivative of pRO1600 which is pRO1614 as carried in NRRL-B-12127.

5. The method of claim 1 including the additional step of conjugally mating the first transconjugant bacterium so as to introduce at least one additional hydrocarbon degradation encoding metabolic plasmid as a second series plasmid with the first series plasmid to produce a second transconjugant bacterium containing at least two hydrocarbon degradation encoding metabolic plasmids which are from the first and second series of such metabolic plasmids.

6. The method of claim 5 wherein the second series transconjugant bacterium comprises the metabolic plasmids CAM, TOL and NPL and has an aliphatic hydrocarbon degrading metabolic function which is not on a plasmid.

7. The method of claim 5 wherein the Pseudomonas for the first series transconjugant is *Pseudomonas aeruginosa* and the second series transconjugant is *Pseudomonas putida*.

8. In a method of introducing hydrocarbon degradation encoding metabolic plasmids into a bacterium of the genus Pseudomonas by transconjugal mating to transmit the plasmid of a donor bacterium to a recipient bacterium to produce a transconjugant bacterium containing the metabolic plasmid, wherein the recipient and donor bacterium are each different nutrient factor auxotrophs the improvement which comprises:
   (a) providing a donor bacterium containing at least one first series hydrocarbon degradation encoding metabolic plasmid;
   (b) providing a recipient bacterium containing a plasmid derivative of pRO1600 as carried in NRRL-B-12124 wherein the plasmid derivative comprises an antibiotic resistance marker not present in the donor bacterium;
   (c) mating the donor bacterium and the recipient bacterium to produce a transconjugant bacterium with the pRO1600 plasmid derivative and the metabolic plasmid; and
   (d) growing the transconjugant bacterium with the nutrient factor required by the recipient bacterium without the nutrient factor required by the donor bacterium in the presence of the antibiotic so as to isolate the transconjugant bacterium with the metabolic plasmid of the donor bacterium and the pRO1600 derivative.

9. The method of claim 8 wherein the pRO1600 derivative is pRO1614 as carried in NRRL-B-12127.

10. The method of claim 8 wherein the pRO1600 derivative is pRO1601 as carried in NRRL-B-12125.

11. The method of claim 8 wherein in addition the transconjugant bacterium is used to donate the metabolic plasmid without the plasmid derivative to a second recipient bacterium.

* * * * *